(12) United States Patent
Alanine et al.

(10) Patent No.: US 7,790,733 B2
(45) Date of Patent: Sep. 7, 2010

(54) 8-ALKOXY OR CYCLOALKOXY-4-METHYL-3,4-DIHYDRO-QUINAZOLIN-2-YLAMINES

(75) Inventors: Alexander Alanine, Schlierbach (FR); Luca Claudio Gobbi, Oberwil (CH); Sabine Kolczewski, Rheinfelden (DE); Thomas Luebbers, Loerrach (DE); Jens-Uwe Peters, Grenzach-Wyhlen (DE); Lucinda Steward, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 1113 days.

(21) Appl. No.: 11/472,084

(22) Filed: Jun. 21, 2006

(65) Prior Publication Data

US 2006/0293350 A1 Dec. 28, 2006

(30) Foreign Application Priority Data

Jun. 27, 2005 (EP) .................................. 05105699

(51) Int. Cl.
*A61K 31/517* (2006.01)
*C07D 239/84* (2006.01)

(52) U.S. Cl. ..................................... 514/266.4; 544/292
(58) Field of Classification Search .............. 514/266.4; 544/292
See application file for complete search history.

(56) References Cited

U.S. PATENT DOCUMENTS 5,693,652 A * 12/1997 Takase et al. ................. 514/322

FOREIGN PATENT DOCUMENTS

WO WO 2004/096771 11/2004
WO WO 2005/042501 A1 5/2005

OTHER PUBLICATIONS

Hoyer et al., Pharmacol. Rev. vol. 46, pp. 157-204 (1994).
Rees, S. et al., FEBS Letters, vol. 355, pp. 242-246 (1994).
Francken et al., Eur. J. Pharmacol. vol. 361, pp. 299-309 (1998).
Noda et al., J. Neurochem. vol. 84, pp. 222-232 (2003).
Dubertret C. et al., The Journal of Psychiatric Research, vol. 38, pp. 371-376 (2004).
Trinka et al., J. Prakt. Chem. vol. 338(7) pp. 675-678 (1996).
Rahman, A. A., et al., Bioorganic & Medical Chemistry Letters, vol. 13, No. 6, 2003, pp. 1119-1123, XP002298657.

* cited by examiner

*Primary Examiner*—James O Wilson
*Assistant Examiner*—Tamthom N Truong
(74) *Attorney, Agent, or Firm*—George W. Johnston; Patricia S. Rocha-Tramaloni; Kimberly J. Prior

(57) ABSTRACT

The present invention relates to compounds of formula

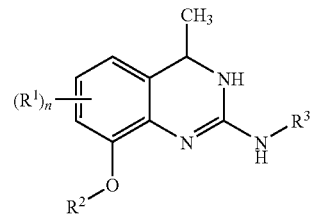

wherein
$R^1$, $R^2$, $R^3$, and
n are as described in the specification and pharmaceutically acceptable acid addition salts thereof. The compounds of formula I can be used for the treatment of $5\text{-HT}_{5A}$ receptor antagonists related diseases, which include depression, anxiety disorders, schizophrenia, panic disorders, agoraphobia, social phobia, obsessive compulsive disorders, post-traumatic stress disorders, pain, memory disorders, disorders of eating behaviors, sexual dysfunction, sleep disorders, withdrawal from abuse of drugs, motor disorders such as Parkinson's disease, dementia in Parkinson's disease, neuroleptic-induced Parkinsonism and tardive dyskinesias, as well as other psychiatric disorders and gastrointestinal disorders such as irritable bowel syndrome.

24 Claims, No Drawings

8-ALKOXY OR CYCLOALKOXY-4-METHYL-3,4-DIHYDRO-QUINAZOLIN-2-YLAMINES

PRIORITY TO RELATED APPLICATIONS

This application claims the benefit European Application No. 05105699.2, filed Jun. 27, 2005, which is hereby incorporated by reference in its entirety.

BACKGROUND OF THE INVENTION

The neurotransmitter 5-hydroxytryptamine (5-HT, serotonin) modulates a wide range of physiological and pathological processes in the central nervous system and periphery, including anxiety, sleep regulation, aggression, feeding and depression (Hoyer et al., *Pharmacol. Rev.* 46, 157-204, 1994). Both pharmacological characterization and molecular cloning of several 5-HT receptor genes has revealed that 5-HT mediates its diverse physiological actions through a multiplicity of receptor subtypes. These receptors belong to at least two different protein superfamilies: ligand-gated ion channel receptor (5-HT$_3$) and the G-protein-coupled 7-transmembrane receptors (thirteen distinct receptors cloned to date). In addition, within the G-protein-coupled receptors, serotonin exerts its actions through a multiplicity of signal transduction mechanisms.

The cloning and characterization of the human 5-HT$_{5A}$ serotonin receptor has been described in *FEBS Letters*, 355, 242-246 (1994). The sequence is not closely related to that of any previously known serotonin receptor, with the best homology being 35% to the human 5-HT$_{1B}$ receptor. It encodes a predicted 357 amino-acid protein, with seven putative transmembrane domains, consistent with that of a G-protein coupled receptor. The sequence is characterized by containing an intron between transmembrane domains V and VI. More recently coupling to Gi/o α mechanisms has been demonstrated with the inhibition of forskolin stimulated cAMP and also evidence for more complicated G-protein mediated coupling mechanisms have been proposed (Francken et al. *Eur. J. Pharmacol.* 361, 299-309, 1998; Noda et al., *J. Neurochem.* 84, 222-232, 2003). Furthermore, in WO 2004/096771 it is described the use of compounds, which are active on the 5-HT$_{5A}$ serotonin receptor for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders. The *Journal of Psychiatric Research*, 38, 371-376 (2004) describes evidence for a potential significant role of the 5-HT$_{5A}$ gene in schizophrenia and more specifically in patients with later age at onset.

SUMMARY OF THE INVENTION

The present invention provides compounds of formula I

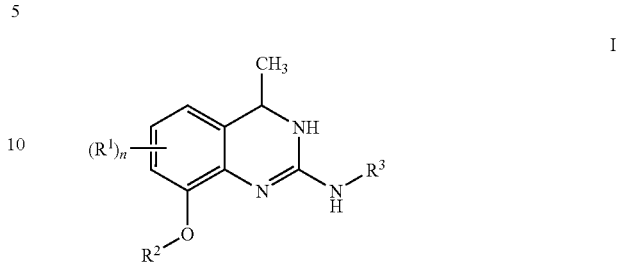

wherein
each $R^1$ is independently hydrogen, halogen or lower alkyl;
$R^2$ is lower alkyl or cycloalkyl;
$R^3$ is hydrogen, lower alkyl, lower alkyl substituted by halogen, cycloalkyl or benzyl optionally substituted by halogen; and
n is 0, 1 or 2;

and pharmaceutically acceptable acid addition salts thereof.

The compounds of formula I can contain asymmetric carbon atoms. Accordingly, the present invention includes all stereoisomeric forms of the compounds of formula I, including each of the individual enantiomers and mixtures thereof.

The present invention also provides pharmaceutical compositions containing one or more compounds of the invention and a pharmaceutically acceptable carrier. The invention further provides methods for the preparation of such compounds and compositions.

Compounds of formula I have good activity on the 5-HT$_{5A}$ receptor. Therefore, the invention provides methods for the treatment of depression (which term includes bipolar depression, unipolar depression, single or recurrent major depressive episodes with or without psychotic features, catatonic features, melancholic features, atypical features or postpartum onset, seasonal affective disorders and dysthymia, depressive disorders resulting from a general medical condition including, but not limited to, myocardial infarction, diabetes, miscarriage or abortion), anxiety disorders, (which includes generalized anxiety and social anxiety disorder, schizophrenia, panic disorders, agoraphobia, social phobia, obsessive compulsive disorders, post-traumatic stress disorders, pain (particularly neuropathic pain), memory disorders (including dementia, amnesic disorders and age-associated memory impairment), disorders of eating behaviors (including nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, ethanol, nicotine, benzodiazepines, alcohol, caffeine, phencyclidine and phencyclidine-like compounds, opiates such as cannabis, heroin, morphine, sedative hypnotic, amphetamine or amphetamine-related drugs), motor disorders such as Parkinson's disease, dementia in Parkinson's disease, neuroleptic-induced Parkinsonism and tardive dyskinesias, as well as other psychiatric disorders and gastrointestinal disorders such as irritable bowel syndrome (WO 2004/096771).

The preferred indications with regard to the present invention are the treatment of anxiety, depression, sleep disorders and schizophrenia.

DETAILED DESCRIPTION OF THE INVENTION

The following definitions of general terms used herein apply irrespective of whether the terms in question appear done or in combination. It should be noted that, as used in the specification and the appended claims, the singular forms "a," "an," and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

The term "cycloalkyl" denotes a saturated hydrocarbon ring containing from 3 to 7 carbon atoms, for example cyclopropyl, cyclopentyl, cyclohexyl and the like.

The term "halogen" denotes chlorine, iodine, fluorine and bromine.

The term "lower alkyl substituted by halogen" denotes a lower alkyl group as defined above, wherein one or more hydrogen atoms is replaced by (a) halogen atom(s), for example $CH_2F$, $CHF_2$, $CF_3$ or the like.

The term "pharmaceutically acceptable" such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

The term "therapeutically effective amount" means an amount that is effective to prevent, alleviate or ameliorate symptoms of disease or prolong the survival of the subject being treated.

The present invention provides compounds of formula I

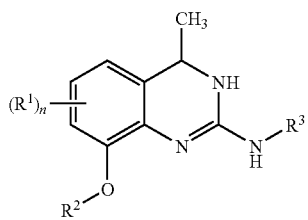

I wherein
each $R^1$ is independently hydrogen, halogen or lower alkyl;
$R^2$ is lower alkyl or cycloalkyl;
$R^3$ is hydrogen, lower alkyl, lower alkyl substituted by halogen, cycloalkyl or is benzyl optionally substituted by halogen; and
n is 0, 1 or 2;

and pharmaceutically acceptable acid addition salts thereof.

The compounds of formula I can contain asymmetric carbon atoms. Accordingly, the present invention includes all stereoisomeric forms of the compounds of formula I, including each of the individual enantiomers and mixtures thereof.

Preferred compounds of formula I are those wherein $R^1$ is hydrogen, in particular those compounds, wherein $R^1$ is hydrogen and $R^2$ is lower alkyl, for example the following compounds:

8-methoxy-4-methyl-3,4-dihydro-quinazolin-2-yl)-amine,
8-isopropoxy-4-methyl-3,4-dihydro-quinazolin-2-yl)-amine,
(2,2-difluoro-ethyl)-(8-ethoxy-4-methyl-3,4-dihydro-quinazolin-2-yl)-amine,
(2,2-difluoro-ethyl)-(8-isopropoxy-4-methyl-3,4-dihydro-quinazolin-2-yl-amine,
(8-isopropoxy-4-methyl-3,4-dihydro-quinazolin-2-yl)-methyl-amine,
(2,2-difluoro-ethyl)-(8-methoxy-4-methyl-3,4-dihydro-quinazolin-2-yl)-amine,
(8-ethoxy-4-methyl-3,4-dihydro-quinazolin-2-yl)-methyl-amine,
8-ethoxy-4-methyl-3,4-dihydro-quinazolin-2-ylamine and
(8-methoxy-4-methyl-3,4-dihydro-quinazolin-2-yl)-methyl-amine.

Preferred compounds of formula I are those, wherein $R^1$ is hydrogen and $R^2$ is cycloalkyl, for example the following compounds:

(8-cyclopentyloxy-4-methyl-3,4-dihydro-quinazolin-2-yl)-methyl-amine and
(8-cyclopentyloxy-4-methyl-3,4-dihydro-quinazolin-2-yl)-(2,2-difluoro-ethyl)-amine.

Further preferred compounds wherein $R^1$ is hydrogen are those wherein $R^3$ is lower alkyl or lower alkyl substituted by halogen. Other such preferred compounds are those wherein $R^3$ is cycloalkyl. Still other such preferred compounds are those wherein $R^3$ is benzyl optionally substituted by halogen.

Preferred compounds of formula I are those wherein $R^1$ is lower alkyl, in particular those compounds wherein $R^1$ and $R^2$ are both lower alkyl. Other preferred compounds wherein $R^1$ is lower alkyl are those wherein $R^2$ is cycloalkyl. Still other such preferred compounds are those wherein $R^3$ is hydrogen. Other preferred compounds wherein $R^1$ is alkyl are those wherein $R^3$ is lower alkyl or lower alkyl substituted by halogen. Further preferred are such compounds wherein $R^3$ is cycloalkyl; also preferred are compounds wherein $R^3$ is benzyl optionally substituted by halogen.

Preferred compounds of formula I are those wherein $R^2$ is alkyl, in particular those compounds wherein each $R^1$ is independently lower alkyl or halogen and $R^2$ is lower alkyl, for example the following compounds:

6-chloro-8-methoxy-4,5-dimethyl-3,4-dihydro-quinazolin-2-yl)-amine,
(6-chloro-8-methoxy-4,5-dimethyl-3,4-dihydro-quinazolin-2-yl)-cyclobutyl-amine and
(6-chloro-8-methoxy-4,5-dimethyl-3,4-dihydro-quinazolin-2-yl)-methyl-amine.

Preferred compounds of formula I are those wherein $R^2$ is cycloalkyl. Other preferred compounds of formula I are those wherein $R^3$ is hydrogen. Still other preferred compounds of formula I are those wherein $R^3$ is cycloalkyl.

Preferred compounds of formula I are those wherein $R^3$ is lower alkyl or lower alkyl substituted by halogen. Other preferred compounds of formula I are those wherein $R^3$ is benzyl optionally substituted by halogen.

The present compounds of formula I and their pharmaceutically acceptable salts can be prepared by methods known in the art, for example by the process described below, which process comprises reacting a compound of formula

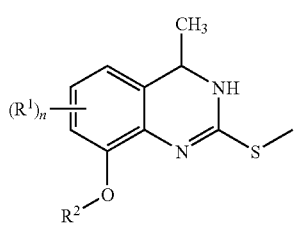

with an amine of formula

  III

R³NH₂ to obtain a compound of formula

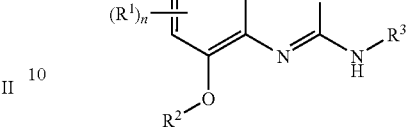  I wherein R¹, R² and R³ and n are as described above, and if desired, converting the compounds obtained into pharmaceutically acceptable acid addition salts.

In examples 1-21 and in the following schemes 1 and 2 the preparation of compounds of formula I are described in more detail. The starting materials are known compounds or can be prepared according to methods known in the art.

Compounds of formula I can be prepared in accordance with the following scheme 1:

Scheme 1

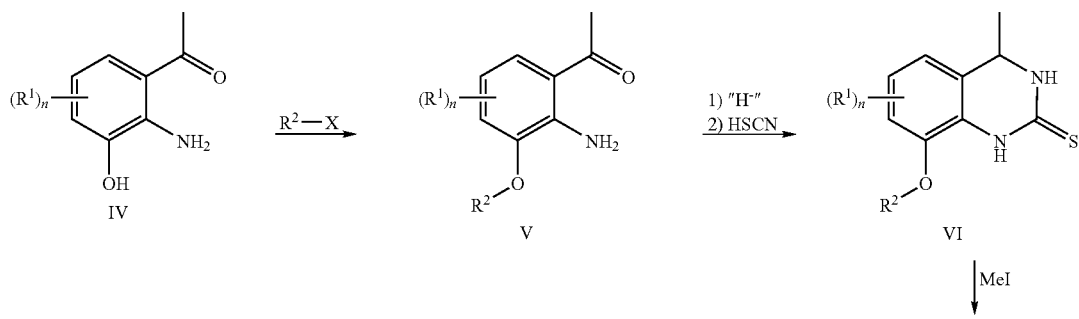

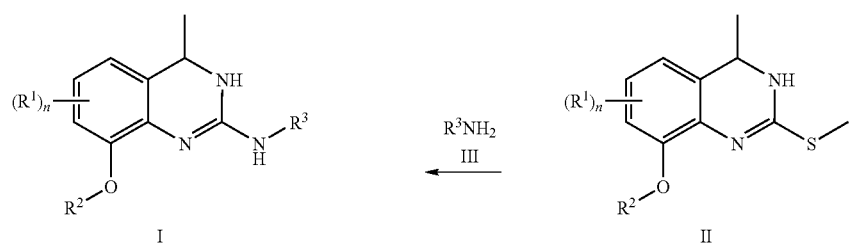

A 2'-amino-3'-hydroxyacetophenone IV is O-alkylated with an alkylating agent, such as an alkyl halide ($R^2X$), optionally in a suitable solvent, such as DMF, optionally in the presence of a base, such as potassium carbonate. The resulting 1-(2-amino-3-alkoxy-phenyl)-ethanone V is reacted with a hydride transfer reagent ("H$^-$"), such as sodium borohydride, optionally in a suitable solvent, such as ethanol, to give an intermediate which can be transformed by HSCN (which can be generated in situ from thiocyanate salt, e.g. KSCN, and an acid, e.g. HCl) to the cyclic thiourea VI. The compound of formula VI is reacted with a methylating agent, such as methyl iodide, optionally in a suitable solvent, such as acetone, to give an 8-alkoxy-4-methyl-2-methylsulfanyl-3,4-dihydro-quinazoliine II, which can usually be isolated as a hydroiodide salt from the reaction mixture by filtration. The compound of formula II is then heated with an amine of formula $R^3NH_2$ optionally in a suitable solvent, such as acetonitrile, optionally in a microwave oven. 8-Alkoxy-4-methyl-3,4-dihydro-quinazolin-2-ylamine I can then be isolated from the reaction mixture by conventional purification.

Alternative the cyclic thiourea VI can be synthesized from the aniline VII via the mono-boc protected 2-bromo-aniline VIII, which can be generated by bromination with a brominating agent, e.g. NBS, optionally in a polar solvent, e.g. acetonitrile, at ambient temperature and subsequent direct mono-boc protection with boc-anhydride optionally in the presence of a base, e.g. DMAP, optionally in a solvent e.g. methylene chloride, or via a two step procedure: di-bocylation with boc-anhydride optionally in a solvent, e.g. THF, at reflux and selective mono-deprotection with a base, e.g. potassium carbonate, optionally in a nucleophilic solvent, e.g. methanol.

Scheme 2

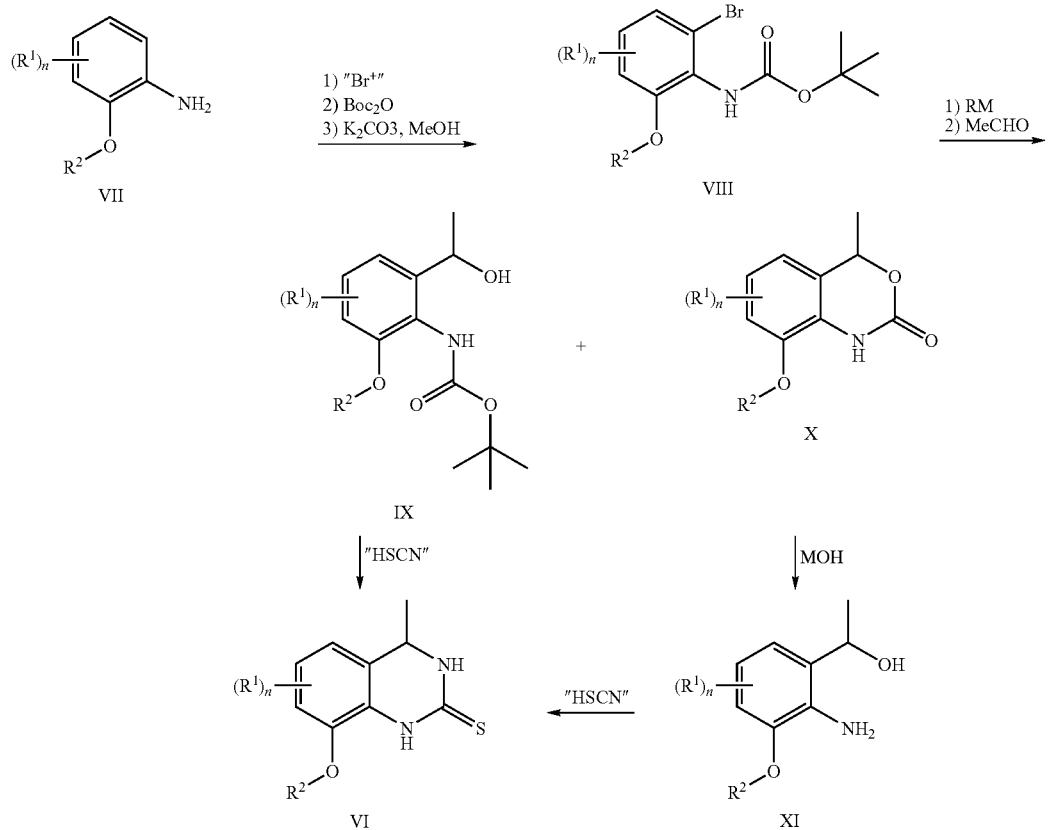

Deprotonation and metal-halogen exchange with an organometallic reagent, e.g. n-BuLi, optionally in a polar solvent, e.g. THF at low temperature and quenching of the organometallic intermediate with acetaldehyde yields either the alcohol derivative IX or the cyclic carbamate X. X can be hydrolyzed with a base, e.g. potassium hydroxide, optionally in a polar solvent, e.g. water/methanol, at higher temperature to the alcohol XI. Both intermediates IX and X can be transferred to the cyclic thiourea VI via the in Scheme 1 described method.

The following abbreviations have been used:
DMF=N,N-dimethylformamide
THF=tetrahydrofuran
DMAP=4-dimethylaminopyridine
RM=metalloorganic reagent
MOH=inorganic hydroxide, such as potassium hydroxide or sodium hydroxide.

Test Description

A [$^3$H]LSD radioligand binding assay was used to determine the affinity of the compounds for the recombinant human 5-HT$_{5A}$ receptor, in membranes from transiently (cDNA) expressed 5-HT$_{5A}$ receptors in Human Embryonic Kidney-EBNA (HEK-EBNA) cells. Assay buffer consisted of Tris (50 mM) buffer containing 1 mM EGTA, 10 mM $MgCl_2$ (pH 7.4) and 10 µM pargyline. The binding assay was carried out in 96-well-plates in the presence of [$^3$H]LSD (approximately 1 nM), approximately 2 µg/well of membrane protein, and 0.5 mg of Ysi-poly-1-lysine SPA beads in a final volume of 200 µl of buffer. Non-specific binding was defined using methiothepin 2 µM. Compounds were tested at 10 concentrations. All assays were conducted in duplicate and repeated at least two times. Assay plates were incubated for 120 min at room temperature before centrifugation. Bound ligand was determined using a Packard Topcount scintillation counter. $IC_{50}$ values were calculated using a non-linear curve fitting program and Ki values calculated using the Cheng-Prussoff equation. The activity of representative compounds (≦0.05 µM) is described in the table below:

| Example | Ki (µM) |
|---|---|
| 1 | 0.00634 |
| 2 | 0.00996 |
| 3 | 0.01409 |
| 4 | 0.02322 |
| 5 | 0.02543 |
| 6 | 0.02816 |
| 7 | 0.0345 |
| 8 | 0.03724 |
| 9 | 0.03844 |
| 16 | 0.01616 |
| 17 | 0.02239 |
| 18 | 0.0047 |
| 19 | 0.0475 |
| 20 | 0.04264 |

The present invention also provides pharmaceutical compositions which comprise one or more compound of the invention and a pharmaceutically acceptable carrier. Such pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, parenterally, e.g. in the form of injectable solutions.

The compositions of the invention, in addition to one or more compounds of the invention, contain a pharmaceutically acceptable carrier. Suitable pharmaceutically acceptable carriers are pharmaceutically inert, inorganic or organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the production of such pharmaceutical compositions. This process comprises bringing one or more compounds of formula I and/or pharmaceutically acceptable acid addition salts and, if desired, one or more other therapeutically valuable substances into a galenical administration form together with one or more therapeutically inert carriers.

As mentioned earlier, the compounds of formula I and their pharmaceutically acceptable addition salts possess valuable pharmaceutical properties. Compounds of the present invention are active on the 5-$HT_{5A}$ receptor and therefore suitable for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

The most preferred indications in accordance with the present invention are those, which include disorders of the central nervous system, for example the treatment of anxiety, depression, sleep disorders and schizophrenia.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | | |
|---|---|---|---|---|---|
| | | mg/tablet | | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | | |
|---|---|---|---|---|---|
| | | mg/capsule | | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Compounds of formula I may be prepared as shown in the following description:

Example 1

8-Methoxy-4-methyl-3,4-dihydro-quinazolin-2-ylamine

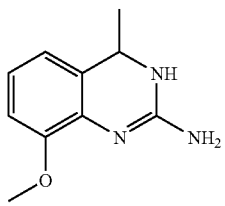

a) 1-(2-Amino-3-methoxy-phenyl)-ethanone

Under an atmosphere of nitrogen, methyl iodide (1.35 g, 10 mmol) and potassium carbonate (4.39 g, 320 mmol) were added to a solution of 2'-amino-3'-hydroxyacetophenone (960 mg, 6 mmol, TCI Europe) in DMF (6 ml). The reaction mixture was stirred for 1 h at r.t., during which time the color of the mixture changed from light brown to dark green. The mixture was then worked up by extraction with $H_2O$/ethyl acetate, drying of the organic phase ($Na_2SO_4$), and evaporation of solvent. The title compound (960 mg, 92%) was isolated from the residue by column chromatography (silica gel, heptan/ethyl acetate=100/0-70/30).

$^1$H NMR (d$^6$-DMSO): δ 2.50 (6H, s), 6.54 (1H, dd), 6.90 (2H, bs), 6.99 (1H, d), 7.36 (1H, d).

b) 8-Methoxy-4-methyl-3,4-dihydro-1H-quinazoline-2-thione

Under an atmosphere of nitrogen and at a temperature of 65° C., sodium borohydride (154 mg, 4 mmol) was added to a solution of 1-(2-amino-3-methoxy-phenyl)-ethanone (960 mg, 6 mmol) in ethanol (8 ml). After stirring at 65° C. overnight, water (5 ml), a solution of potassium thiocyanate (620 mg, 6 mmol) in water (3 ml), and a solution of conc. HCl (3 ml) in water (4 ml) were added subsequently. The mixture was then stirred for an additional 3 h at 65° C. Upon cooling, the solvent was evaporated and the residue was taken up in water/ethyl acetate. The organic phase was dried ($Na_2SO_4$), and the solvent was evaporated. Chromatography (silica gel, heptan/ethyl acetate=100/0-70/30) gave the title compound (700 mg, 58%).

$^1$H NMR (CDCl$_3$): δ 1.53 (3H, d), 3.87 (3H, s), 4.73 (1H, q), 6.66 (1H, d), 6.77 (1H, d), 7.01 (1H, dd), 8.26 (2H, bs).

c) 8-Methoxy-4-methyl-2-methylsulfanyl-3,4-dihydro-quinazoline hydroiodide

Methyl iodide (1.92 g, 14 mmol) was added to a solution of 8-methoxy-4-methyl-3,4-dihydro-1H-quinazoline-2-thione (940 mg, 5 mmol) in acetone (6 ml), and the mixture was stirred for 3 h at r.t. The precipitated title compound (1.2 g, 76%) was filtered off and was used without further purification in the next step.

$^1$H NMR (d$^6$-DMSO): δ 1.43 (3H, d), 2.71 (3H, s), 3.89 (3H, s), 4.97 (1H, q), 6.90 (1H, d), 7.07 (1H, d), 7.25 (1H, dd).

d) 8-Methoxy-4-methyl-3,4-dihydro-quinazolin-2-ylamine

A solution of 8-methoxy-4-methyl-2-methylsulfanyl-3,4-dihydro-quinazoline hydroiodide (610 mg, 1.7 mmol) in a mixture of acetonitrile (6 ml) and aqueous ammonia (25%, 1.2 ml) was heated in a sealed tube on a shaker for 48 h at 80° C. The title compound (158 mg, 46%, MS: m/e=192.1 [M+H$^+$]) was isolated from the reaction mixture by preparative, reverse-phase HPLC (YMC CombiPrep C18 column 50×20 mm, solvent gradient 1-99% CH$_3$CN in 0.05% triethylamine (aq) over 5.0 min, λ=230 nm, flow rate 40 ml/min) as a solid.

Example 2

8-Isopropoxy-4-methyl-3,4-dihydro-quinazolin-2-ylamine

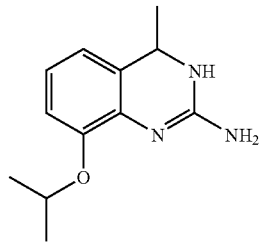

The title compound (MS: m/e=220.3 [M+H$^+$]) was prepared in analogy to example 1 using isopropyl iodide in step a). A microwave oven was used for the heating in step d) [130° C. (15 min) and subsequently 170° C. (30 min)].

Example 3

(2,2-Difluoro-ethyl)-(8-ethoxy-4-methyl-3,4-dihydro-quinazolin-2-yl)-amine

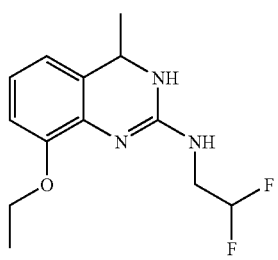

The title compound (MS: m/e=270.4 [M+H$^+$]) was prepared in analogy to example 1 using ethyl iodide in step a). A microwave oven was used for the heating in step d) [130° C. (15 min) and subsequently 170° C. (30 min)].

Example 4

(2,2-Difluoro-ethyl)-(8-isopropoxy-4-methyl-3,4-dihydro-quinazolin-2-yl)-amine

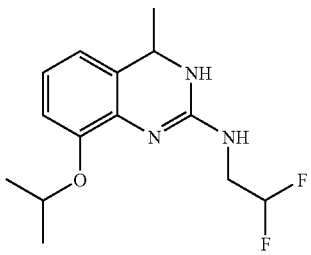

The title compound (MS: m/e=284.3 [M+H$^+$]) was prepared in analogy to example 1 using isopropyl iodide in step a) and 2,2-difluoroethylamine (10 eq.) in step d). A microwave oven was used for the heating in step d) [130° C. (15 min) and subsequently 170° C. (30 min)].

Example 5

(8-Isopropoxy-4-methyl-3,4-dihydro-quinazolin-2-yl)-methyl-amine

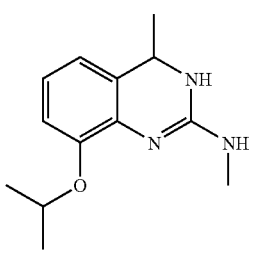

The title compound (MS: m/e=234.3 [M+H$^+$]) was prepared in analogy to example 1 using isopropyl iodide in step a) and methylamine (8M in ethanol, 10 eq.) in step d). A microwave oven was used for the heating in step d) [130° C. (15 min) and subsequently 170° C. (30 min)].

Example 6

(2,2-Difluoro-ethyl)-(8-methoxy-4-methyl-3,4-dihydro-quinazolin-2-yl)-amine

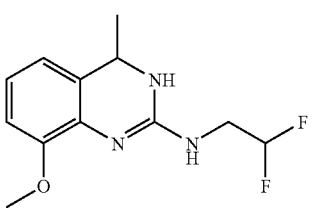

The title compound (MS: m/e=256.4[M+H$^+$]) was prepared in analogy to example 1 using 2,2-difluoroethylamine (10 eq.) in step d).

Example 7

(8-Ethoxy-4-methyl-3,4-dihydro-quinazolin-2-yl)-methyl-amine

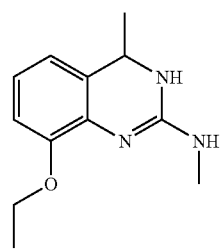

The title compound (MS: m/e=220.3 [M+H$^+$]) was prepared in analogy to example 1 using ethyl iodide in step a) and methylamine (8 M in ethanol, 10 eq.) in step d). A microwave oven was used for the heating in step d) [130° C. (15 min) and subsequently 170° C. (30 min)].

Example 8

8-Ethoxy-4-methyl-3,4-dihydro-quinazolin-2-ylamine

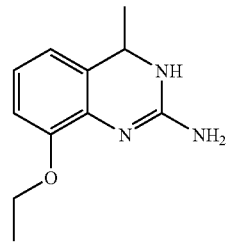

The title compound (MS: m/e=206.2 [M+H$^+$]) was prepared in analogy to example 1 using ethyl iodide in step a). A microwave oven was used for the heating in step d) [130° C. (15 min) and subsequently 170° C. (30 min)].

Example 9

(8-Methoxy-4-methyl-3,4-dihydro-quinazolin-2-yl)-methyl-amine

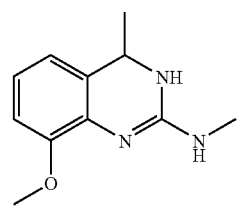

The title compound (MS: m/e=206.1 [M+H$^+$]) was prepared in analogy to example 1 using methylamine (8 M in ethanol, 10 eq.) in step d). A microwave oven was used for the heating in step d) [130° C. (15 min) and subsequently 170° C. (30 min)].

Example 10

Cyclobutyl-(8-isopropoxy-4-methyl-3,4-dihydro-quinazolin-2-yl)-amine

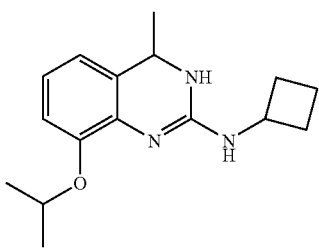

The title compound (MS: m/e=274.4 [M+H$^+$]) was prepared in analogy to example 1 using isopropyl iodide in step a) and cyclobutylamine (10 eq.) in step d). A microwave oven was used for the heating in step d) [130° C. (15 min) and subsequently 170° C. (30 min)].

Example 11

Ethyl-(8-methoxy-4-methyl-3,4-dihydro-quinazolin-2-yl)-amine

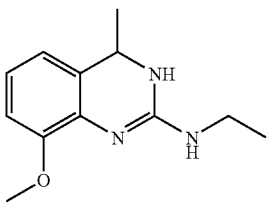

The title compound (MS: m/e=220.3 [M+H$^+$]) was prepared in analogy to example 1 using ethylamine (10 eq.) in step d).

Example 12

Cyclobutyl-(8-methoxy-4-methyl-3,4-dihydro-quinazolin-2-yl)-amine

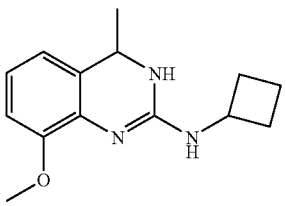

The title compound (MS: m/e=246.3 [M+H$^+$]) was prepared in analogy to example 1 using cyclobutylamine (10 eq.) in step d).

Example 13

Cyclobutyl-(8-ethoxy-4-methyl-3,4-dihydro-quinazolin-2-yl)-amine

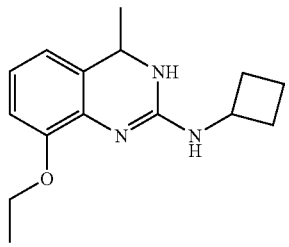

The title compound (MS: m/e=260.1 [M+H$^+$]) was prepared in analogy to example 1 using ethyl iodide in step a) and cyclobutylamine (10 eq.) in step d). A microwave oven was used for the heating in step d) [130° C. (15 min) and subsequently 170° C. (30 min)].

Example 14

[8-(1-Ethyl-propoxy)-4-methyl-3,4-dihydro-quinazolin-2-yl]-methyl-amine

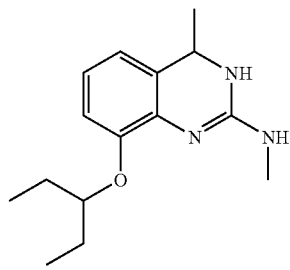

The title compound (MS: m/e=262.3 [M+H$^+$]) was prepared in analogy to example 1 using 3-bromopentane in step a) and methylamine (8M in ethanol, 10 eq.) in step d). A microwave oven was used for the heating in step d) [130° C. (15 min) and subsequently 170° C. (30 min)].

Example 15

(2,2-Difluoro-ethyl)-[8-(1-ethyl-propoxy)-4-methyl-3,4-dihydro-quinazolin-2-yl]-amine

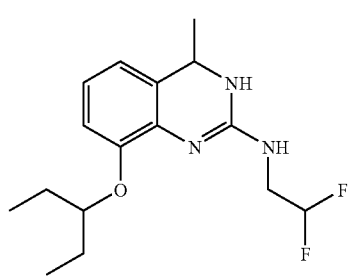

The title compound (MS: m/e=312.3 [M+H$^+$]) was prepared in analogy to example 1 using 3-bromopentane in step a) and 2,2-difluoroethylamine (10 eq.) in step d). A microwave oven was used for the heating in step d) [130° C. (15 min) and subsequently 170° C. (30 min)].

Example 16

(8-Cyclopentyloxy-4-methyl-3,4-dihydro-quinazolin-2-yl)-methyl-amine

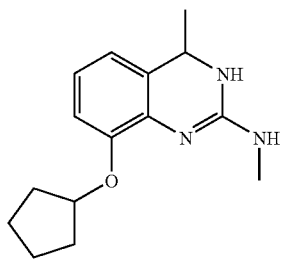

The title compound (MS: m/e=260.3 [M+H$^+$]) was prepared in analogy to example 1 using bromocyclopentane in step a) and methylamine (8M in ethanol, 10 eq.) in step d). A microwave oven was used for the heating in step d) [130° C. (15 min) and subsequently 170° C. (30 min)].

Example 17

(8-Cyclopentyloxy-4-methyl-3,4-dihydro-quinazolin-2-yl)-(2,2-difluoro-ethyl)-amine

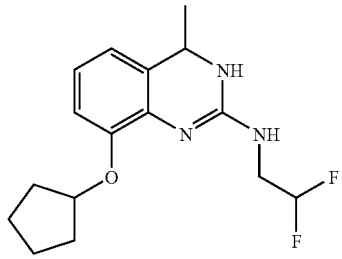

The title compound (MS: m/e=310.4 [M+H$^+$]) was prepared in analogy to example 1 using bromocyclopentane in step a) and 2,2-difluoroethylamine (10 eq.) in step d). A microwave oven was used for the heating in step d) [130° C. (15 min) and subsequently 170° C. (30 min)].

Example 18

6-Chloro-8-methoxy-4,5-dimethyl-3,4-dihydro-quinazolin-2-ylamine

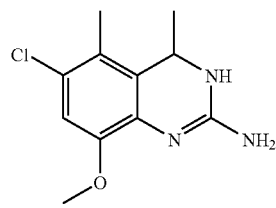

a) 2-Bromo-4-chloro-6-methoxy-3-methyl-phenylamine

N-Bromosuccinimid (3.9 g, 22 mmol) was added to 4-chloro-2-methoxy-5-methylanilin (4.04 g, 20 mmol) dissolved in acetonitril (200 ml). The reaction was stirred at r.t. overnight, and the solvent was evaporated. The residue was purified by column chromatography (silica gel, methylene chloride) to yield the title compound (3.1 g, 62%) as an orange solid.

$^1$H NMR (CDCl$_3$): δ 2.42 (3H, s), 3.84 (3H, s), 4.22 (2H, bs), 6.77 (1H, s).

MS (EI): m/e=249.0/250.9 [M$^+$].

b) N,N-Di(tert-butyloxycarbonyl)-2-bromo-4-chloro-6-methoxy-3-methyl-phenylamine Boc-anhydride (6.1 g, 28 mmol) dissolved in THF (30 ml) was added to 2-bromo-4-chloro-6-methoxy-3-methyl-phenylamine (3.2 g, 12.8 mmol) and DMAP (156 mg, 1.3 mmol) dissolved in THF (100 ml). The reaction was stirred at r.t. overnight, then refluxed for 20 hours. Additionally Boc-anhydride (6.1 g, 28 mmol) and DMAP (156 mg, 1.3 mmol) were added, and the reaction was heated to reflux for 4 hours. The solvent was evaporated, and the residue was dissolved in diethyl ether, washed twice with ice cold 1N aqueous hydrogen chloride solution, once with saturated aqueous sodium chloride solution, dried over sodium sulfate, filtered, and the solvent was evaporated. The residue was stirred with a 1:1 mixture of heptane and diethyl ether for 15 minutes. The product precipitated as a solid and was filtered off (2.5 g). The filtrate was purified by column chromatography (silica gel, heptane/diethyl ether=1/1) to yield the title compound (4.33 g, 75%) as a yellow solid.

$^1$H NMR (CDCl$_3$): δ 1.41 (18H, s), 2.48 (3H, s), 3.80 (3H, s), 6.91 (1H, s).

MS: n/e=450.1/452.2 [M+H$^+$].

c) (2-Bromo-4-chloro-6-methoxy-3-methyl-phenyl)-carbamic acid tert-butyl ester

A suspension of N,N-di(tert-butyloxycarbonyl)-2-bromo-4-chloro-6-methoxy-3-methyl-phenylamine (4.1 g, 9.1 mmol) in methanol (90 ml) was heated to reflux with potassium carbonate (3.77 g, 27 mmol) for 2 days. The reaction was filtered, washed with methanol, and the solvent of the filtrate was evaporated. The residue was dissolved in diethyl ether, washed with cold 1N aqueous hydrogen chloride solution and with saturated sodium chloride solution, dried over sodium sulfate, filtered, and the solvent was evaporated. The residue was stirred for 15 minutes with heptane. The product (2.6 g, 82%) precipitated as an off-white solid and isolated by filtration.

¹H NMR (CDCl₃): δ 1.49 (9H, s), 2.47 (3H, s), 3.83 (3H, s), 5.95 (1H, sb), 6.92 (1H, s).

MS (EI): m/e=349.0/351.1 [M⁺]

d) 6-Chloro-8-methoxy-4,5-dimethyl-1,4-dihydro-benzo[d][1,3]oxazin-2-one n-Butyl lithium (1.6M in hexane, 5.1 ml, 8.1 mmol) was added dropwise under nitrogen at −78° C. to a solution of (2-bromo-4-chloro-6-methoxy-3-methyl-phenyl)-carbamic acid tert-butyl ester (1.3 g, 3.7 mmol) in THF (22 ml). The reaction was stirred for 15 minutes at −78° C., and acetaldehyde (480 ul, 8.4 mmol) was added. The reaction was warmed overnight to r.t. Saturated aqueous ammonium chloride solution (10 ml) was added, the reaction was diluted with water and extracted twice with diethyl ether. The combined organic layers were washed with saturated aqueous sodium chloride solution, dried over sodium sulfate, filtered and the solvent was evaporated. The residue was treated with heptane and little methylene chloride. The title compound was filtered off as a yellow solid. The filtrate was purified by column chromatography (silica gel, heptane/ethyl acetate=1/1) to yield another batch of product, which gave a combined yield of 708 mg (79%).

¹H NMR (CDCl₃): δ 1.56 (3H, d), 2.21 (3H, s), 3.86 (3H, s), 5.60 (1H, q), 6.85 (1H, s).

MS: m/e=242.3 [M+H⁺].

e) 1-(2-Amino-5-chloro-3-methoxy-6-methyl-phenyl)-ethanol 1N aqueous potassium hydroxide solution (13.5 ml, 13.5 mmol) was added to 6-chloro-8-methoxy-4,5-dimethyl-1,4-dihydro-benzo[d][1,3]oxazin-2-one (0.66 g, 2.7 mmol) dissolved in methanol (13.5 ml). The reaction was heated 6 hours to reflux. A solid precipitated. After cooling the reaction was diluted with water, and the title compound was filtered off, washed with water and dried to yield an off-white solid (512 mg, 88%).

¹H NMR (CDCl₃): δ 1.56 (3H, d), 2.26 (3H, s), 3.81 (3H, s), 5.37 (1H, q), 6.72 (1H, s).

MS: m/e=216.4 [M+H⁺].

f) 6-Chloro-8-methoxy-4,5-dimethyl-3,4-dihydro-1H-quinazoline-2-thione

At room temperature and under an atmosphere of nitrogen potassium thiocyanate (262 mg, 2.7 mmol) dissolved in water (2.8 ml) and then concentrated aqueous hydrogen chloride solution (0.7 ml) was added to 1-(2-amino-5-chloro-3-methoxy-6-methyl-phenyl)-ethanol. The reaction was heated for 2 hours to 95° C., cooled and stirred overnight at r.t. The title compound precipitated, was filtered off and washed with water and ethanol to yield a yellow solid (494 mg, 78%).

¹H NMR (d⁶-DMSO): δ 1.20 (3H, d), 2.16 (3H, s), 3.83 (3H, s), 4.56 (1H, mq), 7.05 (1H, s), 8.73 (1H, bs), 9.11 (1H, bs).

MS: m/e=257.3 [M+H³⁰].

g) 6-Chloro-8-methoh-4,5-dimethyl-2-methylsulfanyl-3,4-dihydro-quinazoline hydroiodide Methyl iodide (814 mg, 5.7 mmol) was added to a suspension of 6-chloro-8-methoxy-4,5-dimethyl-3,4-dihydro-1H-quinazoline-2-thione (491 mg, 1.9 mmol) in acetone (5.7 ml), and the mixture was stirred at r.t. overnight. The reaction was diluted with diethyl ether and the precipitated title compound (808 mg, 100%) was filtered off as a white solid and was used without further purification in the next step.

¹H NMR (d⁶-DMSO): δ 1.32 (3H, d), 2.22 (3H, s), 2.71 (3H, s), 3.42 (2H, bs), 3.90 (3H, s), 4.94 (1H, q), 7.23 (1H, s).

MS: m/e=271.3 [M+H⁺].

h) 6-Chloro-8-methoxy-4,5-dimethyl-3,4-dihydro-quinazolin-2-ylamine

6-Chloro-8-methoxy-4,5-dimethyl-2-methylsulfanyl-3,4-dihydro-quinazoline hydroiodide (119 mg, 0.30 mmol) was suspended in a mixture of ammonium hydroxide (0.22 ml, 25% in H₂O, 3 mmol) and acetonitrile (0.9 ml), and heated in a microwave oven to 170° C. (30 min). The reaction was cooled in an ice bath and treated with 1N aqueous sodium hydroxide solution (0.9 ml) and 5-6 drops of concentrated solution of aqueous hydrogen peroxide. A little water was added, and the crude product precipitated and was filtered off. It was purified by column chromatography (silica gel, ethyl acetate/acetone/acetic acid=12/4/1) and was set neutral with 1N aqueous sodium hydroxide solution to yield after drying the title compound as a light grey solid (45 mg, 63%).

¹H NMR (d⁶-DMSO): δ 1.05 (3H, d), 2.11 (3H, s), 3.68 (3H, s), 4.50 (1H, q), 5.70 (2H, bs), 6.72 (1H, s).

MS: m/e=240.1 [M+H⁺].

Example 19

(6-Chloro-8-methoxy-4,5-dimethyl-3,4-dihydro-quinazolin-2-yl)-cyclobutyl-amine

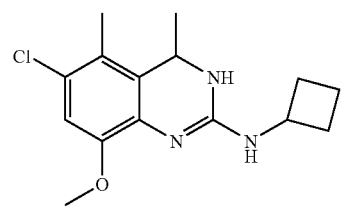

The title compound (MS: m/e=294.1 [M+H⁺]) was prepared in analogy to example 18 using cyclo-butyl amine in step h). No further chromatography was necessary after filtration of the product.

Example 20

(6-Chloro-8-methoxy-4,5-dimethyl-3,4-dihydro-quinazolin-2-yl)-methyl-amine

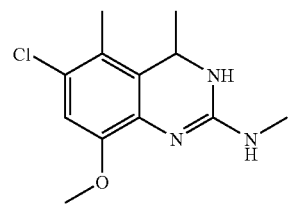

The title compound (MS: m/e=254.3 [M+H$^+$]) was prepared in analogy to example 18 using methyl amine in step h).

Example 21

(2-Chloro-benzyl)-(6-chloro-8-methoxy-4,5-dimethyl-3,4-dihydro-quinazolin-2-yl)-amine

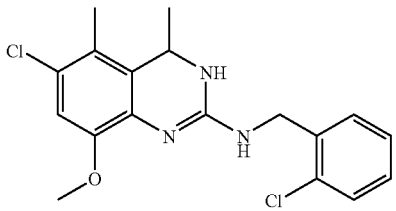

The title compound (MS: m/e=364.3 [M+H$^+$]) was prepared in analogy to example 18 using 2-chlorobenzyl amine (2.5 equivalents) in step h). No further chromatography was necessary after filtration of the product.

The invention claimed is:

1. A compound of formula I

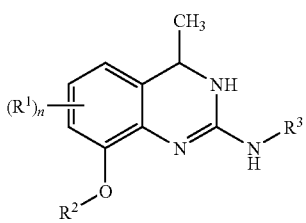

wherein
each R$^1$ is independently hydrogen, halogen or lower alkyl;
R$^2$ is lower alkyl or cycloalkyl;
R$^3$ is hydrogen, lower alkyl, lower alkyl substituted by halogen, cycloalkyl, or benzyl optionally substituted by halogen; and
n is 0, 1 or 2;
or a pharmaceutically acceptable acid addition salt thereof.

2. A compound of claim 1, wherein R$^1$ is hydrogen.

3. A compound of claim 2, wherein R$^2$ is lower alkyl.

4. A compound of claim 3, selected from the group consisting of 8-methoxy-4-methyl-3,4-dihydro-quinazolin-2-ylamine,
8-isopropoxy-4-methyl-3,4-dihydro-quinazolin-2-ylamine,
(2,2-difluoro-ethyl)-(8-ethoxy-4-methyl-3,4-dihydro-quinazolin-2-yl)-amine,
(2,2-difluoro-ethyl)-(8-isopropoxy-4-methyl-3,4-dihydro-quinazolin-2-yl)-amine,
(8-isopropoxy-4-methyl-3,4-dihydro-quinazolin-2-yl)-methyl-amine,
(2,2-difluoro-ethyl)-(8-methoxy-4-methyl-3,4-dihydro-quinazolin-2-yl)-amine,
(8-ethoxy-4-methyl-3,4-dihydro-quinazolin-2-yl)-methyl-amine,
8-ethoxy-4-methyl-3,4-dihydro-quinazolin-2-ylamine and
(8-methoxy-4-methyl-3,4-dihydro-quinazolin-2-yl)-methyl-amine.

5. A compound of claim 2, wherein R$^2$ is cycloalkyl.

6. A compound of claim 5, selected from the group consisting of
(8-cyclopentyloxy-4-methyl-3,4-dihydro-quinazolin-2-yl)-methyl-amine and
(8-cyclopentyloxy-4-methyl-3,4-dihydro-quinazolin-2-yl)-(2,2-difluoro-ethyl)-amine.

7. A compound of claim 2, wherein R$^3$ is hydrogen.

8. A compound of claim 2, wherein R$^3$ is lower alkyl or lower alkyl substituted by halogen.

9. A compound of claim 2, wherein R$^3$ is cycloalkyl.

10. A compound of claim 2, wherein R$^3$ is benzyl optionally substituted by halogen.

11. A compound of claim 1, wherein R$^1$ is lower alkyl.

12. A compound of claim 11, wherein R$^2$ is lower alkyl or cycloalkyl.

13. A compound of claim 11, wherein R$^3$ is hydrogen.

14. A compound of claim 11, wherein R$^3$ is lower alkyl or lower alkyl substituted by halogen.

15. A compound of claim 11, wherein R$^3$ is cycloalkyl.

16. A compound of claim 11, wherein R$^3$ is benzyl optionally substituted by halogen.

17. A compound of claim 1, wherein R$^2$ is alkyl.

18. A compound of claim 17, wherein each R$^1$ is independently halogen or lower alkyl.

19. A compound of claim 18, selected from the group consisting of
6-chloro-8-methoxy-4,5-dimethyl-3,4-dihydro-quinazolin-2-ylamine,
(6-chloro-8-methoxy-4,5-dimethyl-3,4-dihydro-quinazolin-2-yl)-cyclobutyl-amine and
(6-chloro-8-methoxy-4,5-dimethyl-3,4-dihydro-quinazolin-2-yl)-methyl-amine.

20. A compound of claim 1, wherein R$^2$ is cycloalkyl.

21. A compound of claim 1, wherein R$^3$ is hydrogen.

22. A compound of claim 1, wherein R$^3$ is lower alkyl, lower alkyl substituted by halogen, or cycloalkyl.

23. A compound of claim 1, wherein R$^3$ is benzyl optionally substituted by halogen.

24. A pharmaceutical composition comprising a therapeutically effective amount of a compound of formula I

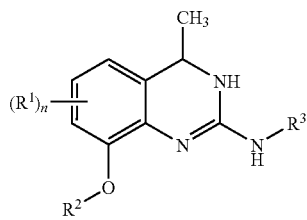

wherein
each R$^1$ is independently hydrogen, halogen or lower alkyl;
R$^3$ is lower alkyl or cycloalkyl;
R$^3$ is hydrogen, lower alkyl, lower alkyl substituted by halogen, cycloalkyl, or benzyl optionally substituted by halogen; and
n is 0, 1 or 2;
or a pharmaceutically acceptable acid addition salt thereof and a pharmaceutically acceptable carrier.

* * * * *